United States Patent [19]
Davis

[11] Patent Number: 5,791,472
[45] Date of Patent: Aug. 11, 1998

[54] SURGICAL TRAY FOR SHARP SURGICAL INSTRUMENTS

[76] Inventor: Mark S. Davis, 4453 Mount Paran Pkwy., Atlanta, Ga. 30327

[21] Appl. No.: 648,989

[22] Filed: May 17, 1996

Related U.S. Application Data

[63] Continuation-in-part of Ser. No. 39,063, May 19, 1995.

[51] Int. Cl.$^6$ ............................................. B65D 83/10
[52] U.S. Cl. .................... 206/370; 206/557; 220/756; 220/606
[58] Field of Search ........................... 206/370, 349, 206/363, 557; 220/756, 771, 606, 608, 607, 912

[56] References Cited

U.S. PATENT DOCUMENTS

| | | |
|---|---|---|
| 114,444 | 5/1871 | Jones . |
| D. 149,518 | 5/1948 | Renoler . |
| 216,346 | 6/1879 | Read . |
| 216,390 | 6/1879 | Furman . |
| D. 226,838 | 5/1973 | Ruskin . |
| D. 276,462 | 11/1984 | Villarrenl . |
| D. 301,167 | 5/1988 | Raybould et al. . |
| D. 345,605 | 3/1994 | Garrow . |
| D. 363,002 | 10/1995 | Douglas . |
| 528,100 | 10/1894 | Hover ............................ 220/756 |
| 1,014,342 | 1/1912 | Marstion . |
| 1,021,425 | 3/1912 | Osom ............................ 220/756 |
| 1,857,372 | 11/1930 | Gleason . |
| 1,913,080 | 1/1932 | Hertner . |
| 2,903,129 | 3/1956 | Anderson, III . |
| 3,032,186 | 5/1962 | Jenkins . |
| 4,183,435 | 1/1986 | Thompson et al. . |
| 4,442,969 | 4/1984 | Holden ........................... 220/608 |
| 4,501,363 | 2/1985 | Isbey, Jr. ........................ 206/363 |
| 4,595,102 | 6/1986 | Cianci et al. ..................... 206/370 |
| 4,717,038 | 1/1988 | Anders ........................... 220/912 |
| 4,834,243 | 5/1989 | Langenbeck ...................... 206/557 |
| 4,889,231 | 12/1989 | Foote et al. ..................... 206/363 |
| 4,917,243 | 4/1990 | Abrams et al. . |
| 4,964,507 | 10/1990 | Chen ............................. 206/557 |
| 4,978,510 | 12/1990 | Smith . |
| 4,982,843 | 1/1991 | Jones . |
| 5,004,109 | 4/1991 | Bartley et al. ................... 220/606 |
| 5,007,535 | 4/1991 | Meseke et al. .................... 206/363 |
| 5,020,665 | 6/1991 | Bruno ............................ 206/370 |
| 5,281,400 | 1/1994 | Berry, Jr. ....................... 206/363 |
| 5,339,955 | 8/1994 | Horan et al. ..................... 206/370 |
| 5,381,896 | 1/1995 | Simons .......................... 206/370 |
| 5,381,901 | 1/1995 | Hundley ......................... 206/457 |
| 5,423,452 | 6/1995 | Tardif ........................... 220/608 |
| 5,441,169 | 8/1995 | Petty ............................ 220/912 |
| 5,520,282 | 5/1996 | Williams, Jr. .................... 206/370 |
| 5,542,533 | 8/1996 | Vargas, III ...................... 206/370 |

OTHER PUBLICATIONS

William Sonoma FAll/Winter Catalog, 1976 Pam Item A p. 43 D7/543.

*Primary Examiner*—B. Dayoan
*Assistant Examiner*—Nhan T. Lam
*Attorney, Agent, or Firm*—Ladas & Parry

[57] ABSTRACT

A surgical tray for transport of a sharp surgical instrument is formed as a shallow, rectangular tray portion with an integral handle extending therefrom. The tray is made as a molded body of relatively lightweight material, such as plastic, and its dimensions are such that the tray portion is adapted to receive a single sharp surgical instrument. The tray portion has a rounded rim at its top end and the handle merges with the rim. The bottom of the tray portion can be formed with ribs to prevent slippage. The upper surface of the bottom of the tray portion can be formed with ribs to facilitate engagement and removal of the sharp instrument. The end of the handle can be flared to prevent slippage of the handle from the hand of the user.

6 Claims, 5 Drawing Sheets

SURGICAL TRAY FOR SHARP SURGICAL INSTRUMENTS

This application is a continuation-in-part of copending application No. 29/039,063 filed on May 19, 1995.

FIELD OF THE INVENTION

The invention relates to a shallow surgical tray for sharp surgical instruments and to its method of use.

BACKGROUND AND PRIOR ART

In the course of conducting surgical operations, numerous sharp surgical instruments need to be transferred between personnel such as between surgeons and surgical assistants, scrub nurses and scrub technicians. The surgical instruments known as "sharps" include suture needles, hypodermic syringe needles, scalpels, wires, sharp retractors and other sharp instruments.

It is of great importance to prevent injuries and resultant spread of blood-borne diseases such as AIDS and hepatitis between the patients and the medical personnel.

Articles which are in current use to transfer "sharps", include mats with or without magnets, basins, pans, trays, clingy cloths and the like. However, such articles lack an integrated handle or other means by which the device with the sharp therein can be held at a safe distance between the hand of the user and the sharp end of the instrument being passed to the surgeon or other medical personnel.

U.S. Pat. No. 2,903,129 shows an instrument tray adapted for supporting a plurality of instruments in an orderly placement in the tray. The tray is not intended for orderly transfer of an instrument between medical personnel and accordingly lacks a suitable handle for this purpose. The tray is intended more as a receptacle for storing a plurality of different instruments for selected use during a surgical procedure.

A similar type of tray for surgical instruments is shown in design U.S. Pat. No. 276,462 and the comments above apply equally hereto as well.

SUMMARY OF THE INVENTION

An object of the invention is to provide a surgical tray for transfer of sharp surgical instruments between medical personnel which minimizes any danger of contact between the surgical instrument and the hand of a user.

A further object of the invention is to provide such a surgical tray having an integrated handle which provides a safe distance between the hand of the user and the sharp end of the surgical instrument being transferred.

A further object of the invention is to provide such a tray with an integrated handle which permits the transfer of the surgical instruments in an unlimited choice of locations within the surgical field.

A further object of the invention is to provide a surgical tray which is relatively inexpensive and is used once after which the tray is discarded.

In accordance with the above and other objects, the invention provides a surgical tray for transporting sharp surgical instruments comprising a rectangular tray portion of relatively lightweight material such as plastic material, whose length is greater than its width and both are greater than its height to provide a relatively narrow and shallow configuration for the tray portion which enables it to receive a single sharp surgical instrument, and a handle portion secured to the tray portion and extending therefrom in the length direction of the tray portion, said handle portion being narrower than said tray portion and having a length substantially exceeding the width of said tray portion and of such dimension to enable a user to hold said handle portion and keep said tray portion at a distance from the hand of the user. The tray portion has a rounded rim at its top end at which the handle portion merges with the tray portion.

In further accordance with the invention, the handle portion is integral with the tray portion and extends therefrom in a common plane therewith.

In further accordance with the invention, the handle portion and tray portion are molded as a single body of plastic material in which the tray portion has side and end walls of a thickness of about 1/32" and the handle portion has a thickness of about 1/4".

In further accordance with the invention, the tray portion has an outer undersurface with means thereon for preventing slippage of said tray when placed on a support surface.

In further accordance with the invention, the tray portion has an inner upper surface with means thereon for facilitating engagement by a user of the sharp surgical instrument.

In further accordance with the invention, the handle portion includes a flared end portion to prevent slippage of the hand of the user from the handle portion.

In further accordance with the invention, the handle portion includes a downward projection at an end of the handle, said downward projection having a height so that the surgical tray is supported in a level position when placed on a horizontal support surface.

A further object of the invention, is to provide a method for transferring sharp surgical instruments between medical personnel.

In accordance with the above object, the invention contemplates a method which comprises placing a sharp surgical instrument in a shallow tray portion of a surgical tray and holding the surgical tray in the hand of a user by engaging a handle portion integral with the tray portion such that the tray portion and surgical instrument are spaced from the hand of the user. The instrument is then transported in the tray by the user, while engaging the handle to a medical person for removal of the instrument from the tray and use of said instrument.

In further accordance with the method of the invention, the tray is formed of lightweight molded plastic in which the handle portion and tray portion are integral and the tray is used only once to transport the surgical instrument after which the tray is discarded.

BRIEF DESCRIPTION THE FIGURES OF THE DRAWING

FIG. 1 a top perspective view of a shallow surgical tray according to the invention.

DETAILED DESCRIPTION OF PREFERRED EMBODIMENTS

Figure 1:
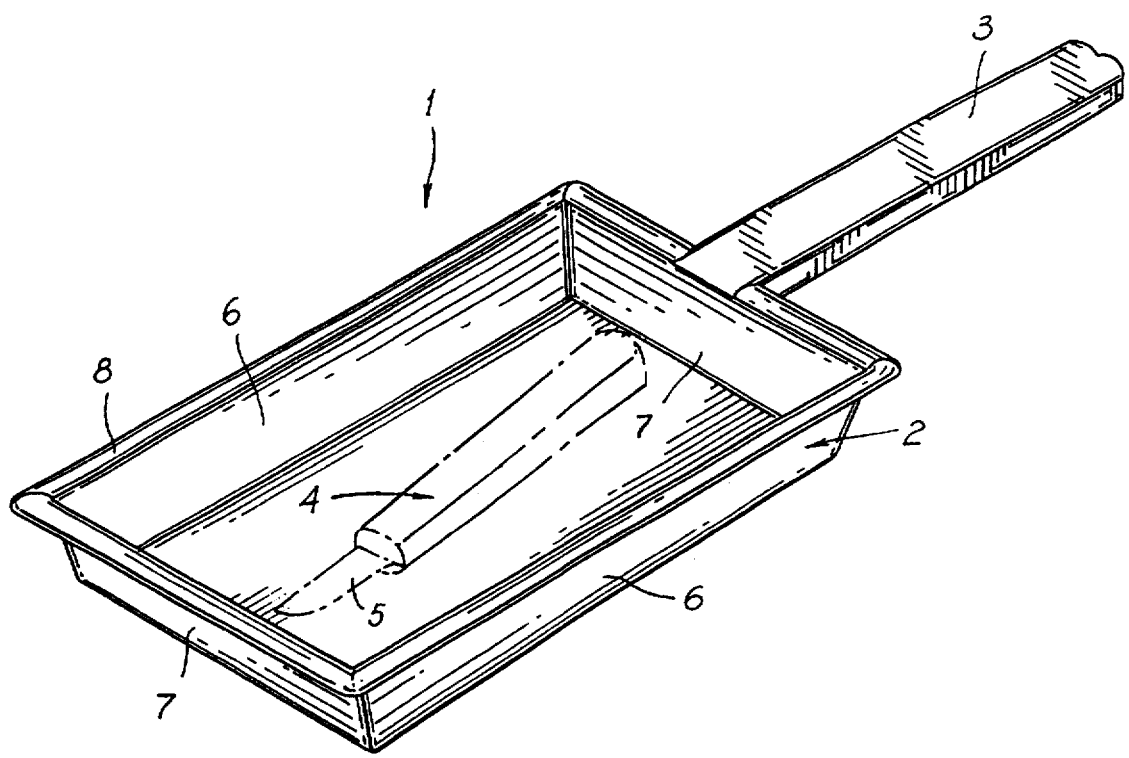
Figure 2:
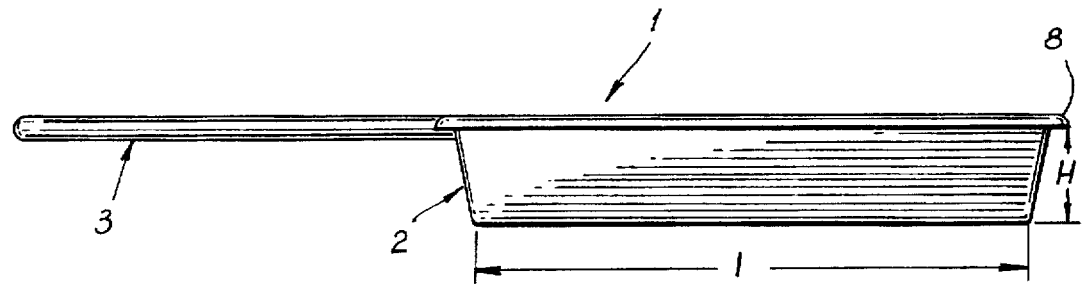
FIG. 2 is a right side elevational view of the tray.
Figure 3:
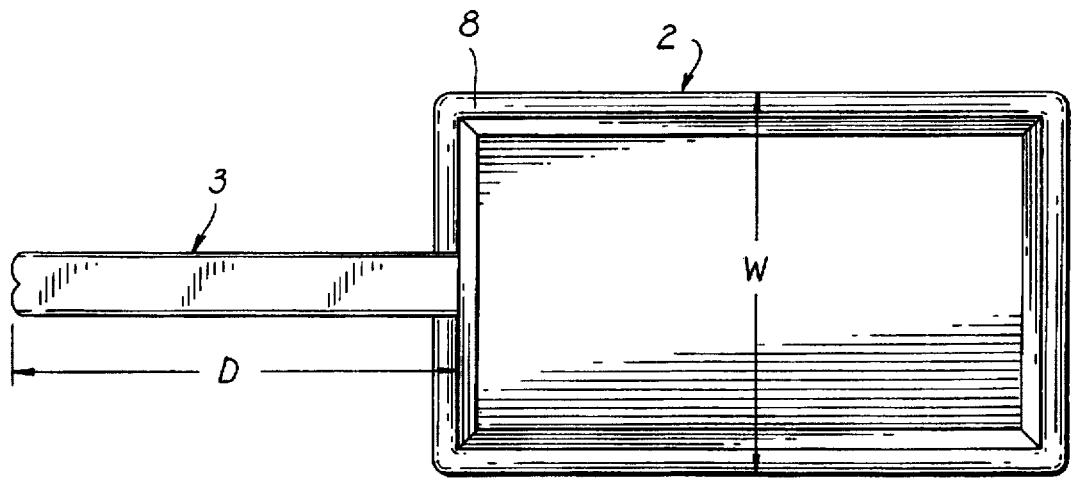
FIG. 3 is a top plan view of the tray.
Figure 4:
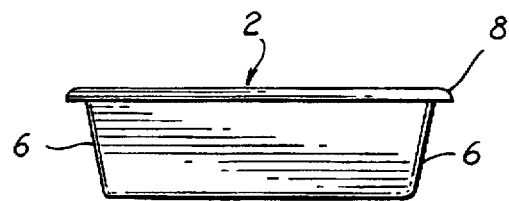
FIG. 4 is an elevational view of the tray from the end thereof without the handle.
Figure 5:
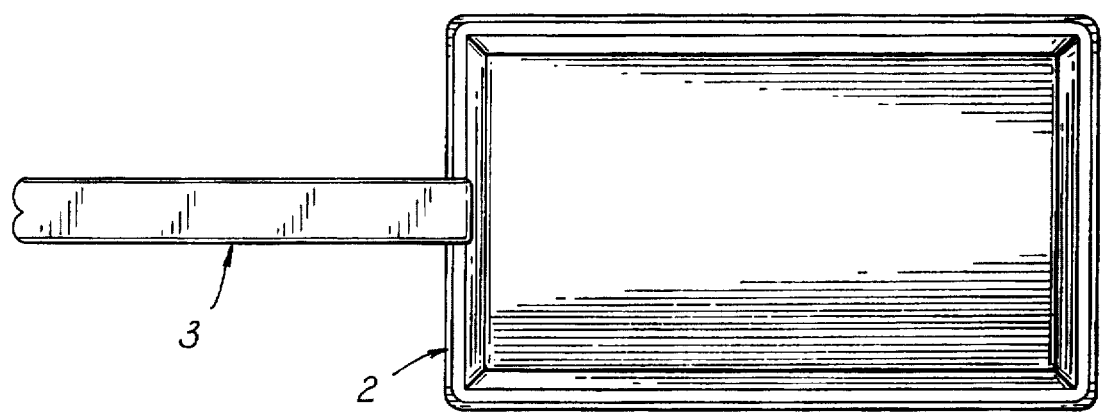
FIG. 5 is a bottom plan view of the tray.
Figure 6:
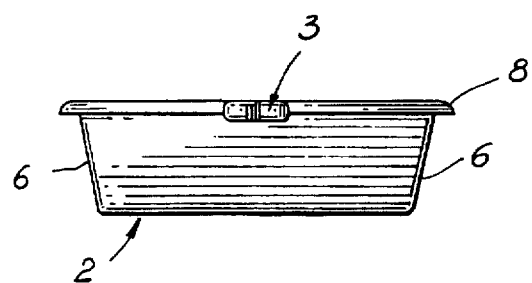
FIG. 6 is an elevational view of the tray from the end with the handle.
Figure 7:
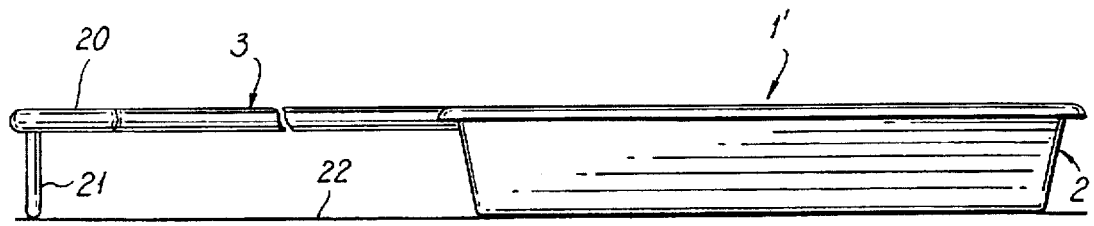
FIG. 7 is a view similar to FIG. 2 of a modified embodiment of the trap
Figure 8:
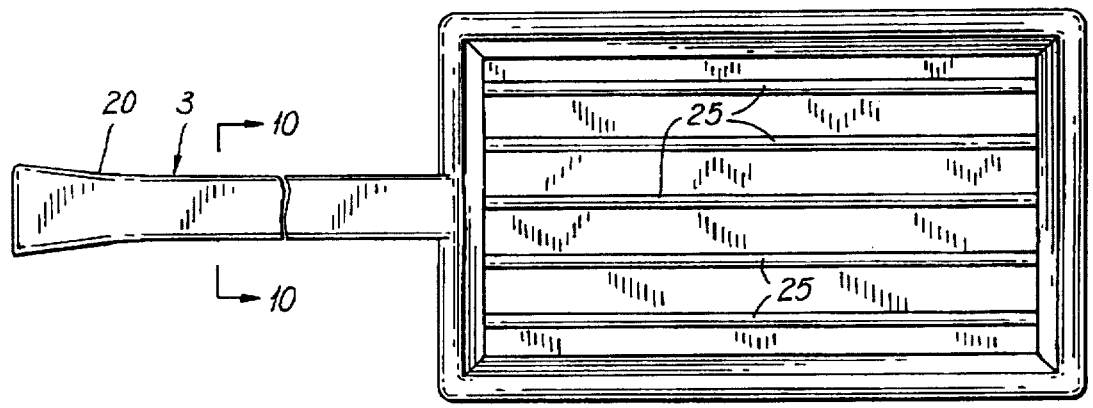
FIG. 8 is a top plan view of the embodiment of FIG. 7.
Figure 9:
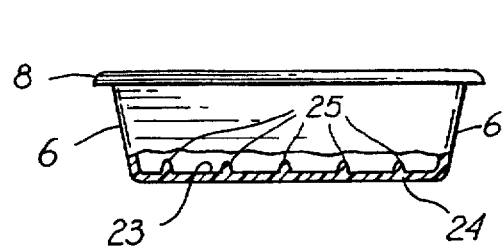
FIG. 9 is an end view, partly broken away and in section, of the embodiment of FIG. 7.

Referring to FIGS. 1–6 of the drawing, therein is seen a shallow surgical tray 1 according to the invention which comprises a tray portion 2 to which is secured a handle portion 3. Shown within the tray portion 2, is a surgical instrument 4 in the form of a scalpel having a sharp blade 5. The tray portion 2 includes opposed side walls 6 and opposed end walls 7. The side walls 6 and end walls 7 are slightly tapered and widen upwardly. At a top end of the walls, the tray portion is formed with a rounded rim 8 which extends entirely around the perimeter of the tray. The rounded rim 8 facilitates insertion and removal of the instrument 4 by the users of the tray.

The handle portion 3 is integral with the tray portion at the rim and extends substantially in a common plane with the rim.

The tray portion 2 has a length dimension L, which exceeds the width dimension W whereby the tray portion has a relatively narrow, rectangular configuration. The height dimension H of the tray portion is substantially less than the width dimension W so that the tray portion 2 is relatively shallow. The handle portion 3 is elongated and extends in the length direction of the tray portion over a distance D. The distance D is greater than the dimension W and less than the dimension L of the tray portion. Thereby, a user of the tray is able to hold the handle portion 3 and keep the tray portion 2 at a distance from the hand of the user. In this way, the handle portion provides a safe distance between the hand of the user and the sharp end 5 of the instrument when the instrument is being passed to a surgeon or other user. Additionally, the tray may be safely and conveniently repositioned by engaging the handle portion at any time during a surgical procedure for the convenience of one or more surgeons requiring access to a sharp instrument during the surgical procedure.

In a particularly advantageous use in a procedure such as a vaginal hysterectomy or other vaginal surgery where the assisting nurse is positioned behind the operating surgeon, and the passing of sharp instruments can be dangerous because the sharp instrument must be passed from behind the surgeon, the tray of the invention eliminates this danger. In this respect, the assisting nurse or technician can safely access the surgical field in front of the surgeon because of the ability to position the tray in front of the surgeon due to the presence of the handle portion on the tray.

The invention contemplates forming the tray as a molded body in which the tray portion 2 and the handle portion 3 are integrally formed. The tray can be made of an inexpensive plastic material, such as polypropylene, polyethylene terephthalate, styrene or the like, so that it can be used once and discarded.

In a typical embodiment, the thickness of the walls 6 and 7 and the top rim 8 is 1/32" and the thickness of the handle is 1/4". The length dimension L of the tray portion is 8½ inches, the width dimension W is 4¾ inches and the height dimension H is 1¾ inches. The handle has a length dimension D of 6 inches and a width of 1 inch. Thus, the length dimension D of the handle is greater than two-thirds the length dimension L of the tray portion and the width dimension W of the tray portion is less than two-thirds the length dimension L.

The dimensions of the tray are such that the tray can carry a single surgical instrument and although a scalpel has been shown by way of example in FIG. 1, other suitable surgical instruments include suture carriers loaded with suture needles, sharp retractors, sharp ended wires and other similar instruments which could cause injury to the medical personnel handling the same.

FIGS. 7—10 show a further embodiment of the tray designated by numeral 1'. Elements of the tray 1' similar to those in the embodiment of FIGS. 1—6 have the same reference characters. Thus, the tray 1' is formed with the tray portion 2 and the integral handle 3. The handle 3 of the tray 1', has a flared end 20 which prevents slippage of the handle from the hand of the user. At the end of the flared end 20, the handle is formed with a vertical depending projection 21 of a length such that when the tray 1' is placed on a level surface 22, the projection 21 will contact the surface 22 and stabilize the tray 1' in its position on the support surface.

In a variation, the tray portion 2 is provided at the inside upper surface 23 of the bottom wall 24 with a plurality of upstanding ribs 25 constituting means for holding the surgical instrument in an elevated position above the bottom of the tray to facilitate engagement of the surgical instrument by the user.

Figure 10:
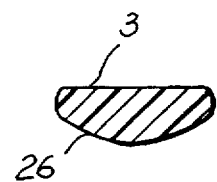
FIG. 10 is a sectional view taken along line 10—10 in FIG. 8.

In another modification as shown in FIG. 10, the underside of the handle portion 3 is rounded as shown at surface 26 to facilitate handling of the tray by the user and provide comfort for the hand of the user.

Figure 11:
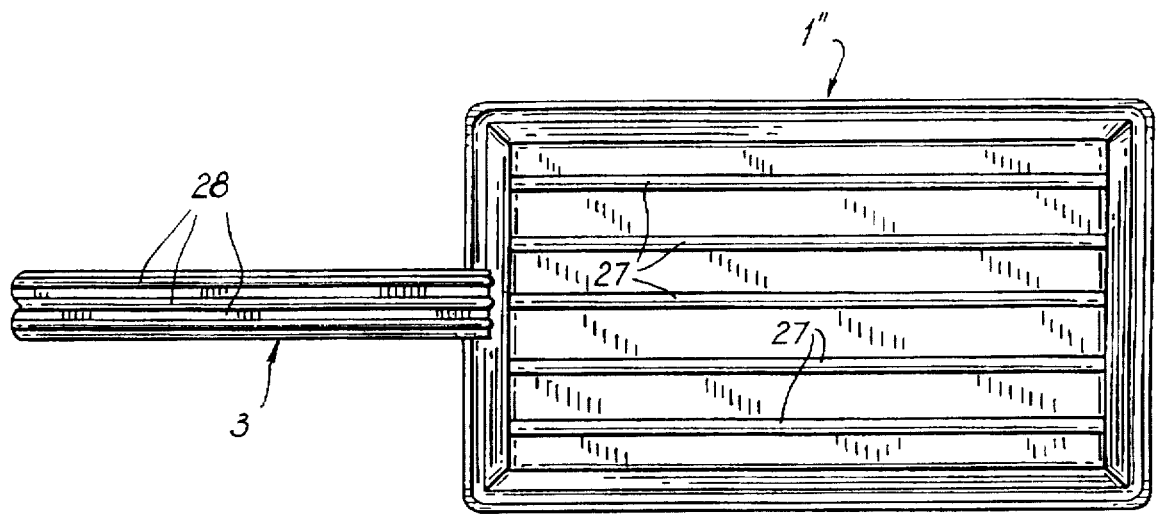
FIG. 11 is a view similar to FIG. 5 of another modified embodiment of the tray.
Figure 12:
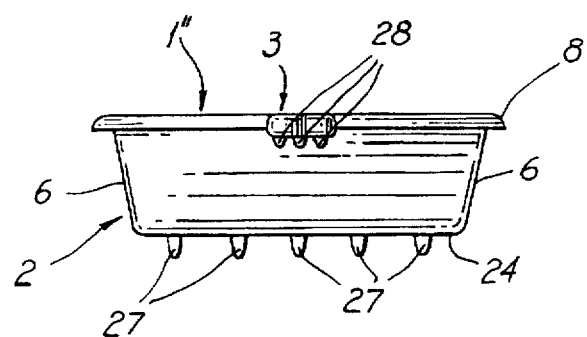
FIG. 12 is an end view of the embodiment in FIG. 11.

FIGS. 11 and 12 show another embodiment of the tray 1" in which the same reference characters are used to designate the same elements. The tray 1" is formed at the underside of the bottom 24 of the tray portion with a plurality of ribs 27 serving as a means to prevent slippage of the tray when placed on a support surface. In order to reinforce the handle portion 3, ribs 28 are formed on the undersurface of the handle portion 3. The ribs 28 are shown extending longitudinally but transverse ribs can be provided at spaced locations as well.

Although the invention has been described in relation to specific embodiments thereof, it will become apparent to those skilled in the art that numerous modifications and variations can be made within the scope and spirit of the invention as defined in the attached claims.

Thus, for example, the tray could also be made of metal and re-used with intervening sterilization. However, this is relatively costly and it is preferred to make the tray of plastic material and use it only once. Also, when the tray is made of plastic there is no danger of damaging the sharp instruments upon impact with the tray during normal handling.

What is claimed is:

1. A surgical tray for transfer of a sharp surgical instrument comprising:

a rectangular tray portion of relatively lightweight material, said tray portion having long side walls and short end walls providing length and width dimensions of said tray portion greater than a height dimension of said tray portion to provide an elongated, relatively shallow configuration for said tray portion to receive a sharp surgical instrument, and a handle portion secured to one of said short end walls of said tray portion and extending therefrom in the direction of the long side walls of said tray portion, said handle portion having a width which is less the width dimension of said tray portion and having a length exceeding the width dimension of said tray portion and greater than two thirds the length dimension of the tray portion, to enable a user to hold said handle portion and keep said tray portion at a distance from the hand of the user with the length dimension of the tray portion in extension of said handle portion, said width dimension of said tray portion being less than two-thirds said length dimension of said tray portion, said tray portion including a rounded rim at a top end thereof, said handle portion merging with said rim, said handle portion being integrally molded with said tray portion and extending from said rim in a common plane therewith, said tray portion having an outer undersurface with means thereon for preventing slippage of said tray when placed on a support surface, said tray portion having a bottom wall with an inner, upper surface with means thereon for facilitating engagement by a user of the sharp surgical instrument in the tray portion, said handle portion including a downward projection at an end of the handle portion, said downward projection having a height so that the surgical tray is supported in a level position when placed on a horizontal support surface.

2. A surgical tray as claimed in claim 1, wherein said tray is made of plastic material.

3. A surgical tray as claimed in claim 1, wherein said handle portion is rectangular.

4. A surgical tray as claimed in claim 1, wherein said side and end walls taper and widen upwardly.

5. A surgical tray as claimed in claim 2, wherein said side and end walls having a thickness of 1/32".

6. A surgical tray as claimed in claim 1, wherein said handle portion includes a flared end portion to prevent slippage of a hand of the user from said handle portion.

* * * * *